United States Patent
Izumo et al.

(10) Patent No.: US 10,067,046 B2
(45) Date of Patent: Sep. 4, 2018

(54) CONTAINMENT WORKSTATION FOR HAZARDOUS FINE PARTICLES

(71) Applicant: A&D Company, Limited, Tokyo (JP)

(72) Inventors: Naoto Izumo, Saitama (JP); Shunsuke Kasamatsu, Saitama (JP)

(73) Assignee: A&D COMPANY, LIMITED, Tokyo (JP)

( * ) Notice: Subject to any disclaimer, the term of this patent is extended or adjusted under 35 U.S.C. 154(b) by 93 days.

(21) Appl. No.: 15/116,134

(22) PCT Filed: Feb. 3, 2014

(86) PCT No.: PCT/JP2014/052443
§ 371 (c)(1),
(2) Date: Aug. 2, 2016

(87) PCT Pub. No.: WO2015/114831
PCT Pub. Date: Aug. 6, 2015

(65) Prior Publication Data
US 2017/0219474 A1  Aug. 3, 2017

(51) Int. Cl.
*G01N 1/22* (2006.01)
*G01N 15/06* (2006.01)
*G01N 1/24* (2006.01)

(52) U.S. Cl.
CPC ....... *G01N 15/0618* (2013.01); *G01N 1/2273* (2013.01); *G01N 1/24* (2013.01);
(Continued)

(58) Field of Classification Search
CPC .... G01N 15/0618; G01N 1/2273; G01N 1/20; G01N 1/24; G01N 1/2205; G01N 2001/2288; G01N 2001/245
See application file for complete search history.

(56) References Cited

U.S. PATENT DOCUMENTS

| 5,505,848 A * | 4/1996 | Landine | B01D 21/0027 |
| | | | 210/170.08 |
| 2008/0173362 A1 * | 7/2008 | Wong | F15B 1/26 |
| | | | 137/574 |
| 2013/0306382 A1 * | 11/2013 | Izumo | G01G 23/01 |
| | | | 177/25.14 |

FOREIGN PATENT DOCUMENTS

JP   56-047741      9/1979
JP   56-047741 U1   4/1981
(Continued)

OTHER PUBLICATIONS

International Search Report and International Preliminary Examination Report PCT/JP2014/052443 dated Feb. 25, 2014.
(Continued)

*Primary Examiner* — Harshad R Patel
*Assistant Examiner* — Nigel Plumb
(74) *Attorney, Agent, or Firm* — Roberts Mlotkowski Safran Cole & Calderon, P.C.

(57) ABSTRACT

Provided is a measuring system capable of stably, safely, and easily measuring hazardous fine particles. A measuring system 10 includes a work space 3 in which measuring equipment 5 can be installed, a containment device 13 that defines the work space 3 by closing portions other than an open section 134 and an air inlet 132 and an air outlet 133, a temperature and humidity control device 11, a filter unit 12, and a first connection means 14, a second connection means 15, and a third connection means 16 that connect the above-described components. Accordingly, in the measuring system 10, air whose temperature and humidity are controlled circulates, and a laminar flow flows in the work space 3, and particles floating in the work space 3 are reliably contained inside the measuring system 10.

3 Claims, 9 Drawing Sheets

(52) U.S. Cl.
CPC .............. *G01N 2001/2288* (2013.01); *G01N 2001/245* (2013.01)

(56) References Cited

FOREIGN PATENT DOCUMENTS

| | | | |
|---|---|---|---|
| JP | 06-233941 | | 8/1994 |
| JP | 2004-090174 | | 3/2004 |
| JP | 2006-074268 | | 3/2006 |
| JP | 2006-122816 | | 5/2006 |
| JP | 2006112816 | * | 5/2006 |
| JP | 2009-030857 | | 2/2009 |

OTHER PUBLICATIONS

Microfilm of the specification and drawings annexed to the request of Japanese Utility Model Application No. 128637/1979 (Laid-open No. 47741/1981) Taiyo Kagaku Kogyo Kabushiki Kaisha Apr. 28, 1981.

* cited by examiner

CONTAINMENT WORKSTATION FOR HAZARDOUS FINE PARTICLES

TECHNICAL FIELD

The present invention relates to a measuring system in which measuring equipment such as a scale is disposed, and in particular, to a measuring system to measure hazardous fine particles.

BACKGROUND ART

In recent years, the presence of dust that has harmful effects on the human body when a human breathes it in has become a social problem. Such dust includes various substances, for example, suspended particulate matter such as fine particulate matter (PM2.5), asbestos known as a substance that causes lung cancer, silica, carbon nanotube, and anticancer drugs. At a site to study and analyze these hazardous particles, these substances are handled at high concentrations for long periods of time, so that researchers and operators are in an environment with a higher risk of being exposed to these hazardous substances.

In particular, with a mass concentration measurement of PM2.5, there is a need to attach a filter to a prescribed collection device installed in the atmosphere, and measure the weight of particulate matter collected by this filter. At this time, for stable measurement by preventing adsorption of particulate matter due to moisture absorption of the filter, there are standards strictly limiting a measuring environment to a temperature of 21.5±1.5° C., humidity of 35±5%, and scale accuracy of ±1 µg. Therefore, a space in which a scale is installed must be controlled so that the temperature and humidity fall within the standards.

FIG. 9 is a schematic view of a scale chamber realizing constant temperature and constant humidity, conventionally used for measuring hazardous particles such as PM2.5. Reference sign 1 denotes a main body of a temperature and humidity control device, reference sign 2 denotes an indoor equipment of a temperature and humidity control device, reference sign 3 denotes a work space, reference sign 4 denotes a heat-insulated chamber covering the scale chamber, and reference sign 5 denotes a scale. The arrow shows airflow. That is, after the scale chamber is insulated and the work space 3 is changed into a uniform environment by generating air blow whose temperature and humidity are managed by the temperature and humidity control devices 1 and 2, measuring is performed.

However, this environment creation has a problem in which, there is a need for considerable capital investment, and a measured value of the scale 5 becomes unstable due to strong air blow for agitating air inside a room sufficiently large for a person to enter. A further problem is that hazardous particles are disturbed by the air blow and scatter in the work space 3, and an operator becomes exposed to the hazardous particles.

On the other hand, as systems that prevent exposure to hazardous particles, a glove box (for example, refer to Patent literature 1) by which hazardous substances are contained in an enclosed space and handled via gloves, and a draft chamber (for example, refer to Patent literature 2) that forcibly exhausts air from a work space and forcibly suctions the hazardous substances to prevent it from flowing outside, are known.

CITATION LIST

Patent Literatures

Patent Literature 1: Japanese Unexamined Patent Application Publication No. 2004-090174 (FIG. 1, etc.)
Patent Literature 2: Japanese Unexamined Patent Application Publication No. 2005-074268 (FIG. 1, etc.)

SUMMARY OF THE INVENTION

Problem to be Solved by the Invention

However, realistically, the glove box has a problem in which the degree of freedom of operation of the glove box is low since an enclosed space is formed, and the glove box is used in limited situations for operation of hazardous virus.

The draft chamber has a mechanism that suctions and exhausts hazardous substances in the work space, however, only a high exhaust performance is prescribed, and a function to contain particulate hazardous substances being particles is not guaranteed. In addition, as equipment in the device structure, an exhaust tube connected to the line of the chamber is necessary, and this tube and its surrounding increase the initial investment and make difficult new installation at an arbitrary location. Further, since the draft chamber performs forced exhaust, so that the airflow inside the chamber is turbulent, and when a scale is installed, it becomes difficult to settle a measured value in many cases. This problem becomes even more unignorable when a high-accuracy scale is installed.

As described above, at present, it is difficult to perform measurement with no exposure to humans without difficulties (including cost and the degree of freedom of installation of the device) while balancing conflicting conditions that a uniform measuring environment is realized and a measured value of a high-accuracy scale is stabilized.

The present invention has been made to solve the above-described problems in conventional technologies, and an object thereof is to provide a measuring system for measuring hazardous fine particles stably, safely, and easily.

Means for Solving the Problems

In order to accomplish the above-described object, a measuring system according to the present invention includes a work space in which measuring equipment can be installed, a containment device that defines the work space by closing portions other than an open section provided in the front surface of the work space, and an air inlet and an air outlet set in the work space, a temperature and humidity control device that controls a temperature and a humidity of taken-in air and can blow the air into the work space, a filter unit that collects particles, a first connection means that hermetically connects the temperature and humidity control device and the air inlet of the containment device, a second connection means that hermetically connects the air outlet of the containment device and the filter unit, and a third connection means that hermetically connects the filter unit and the temperature and humidity control device.

With this configuration, air whose temperature and humidity are controlled, fed-out from the temperature and humidity control device is guided to the containment device via the first connection means. In the containment device, the air is flowed into the work space from the air inlet set in the containment device, and discharged from the air outlet set in the containment device. At this time, in the work space, designed airflow is generated, and a negative pressure relative to the outside is generated in the open section of the containment device which is the only open space in the measuring system. As a result, the air flowed into the work space is guided to the filter unit via the second connection means together with outside air flowed into the work space from the open section provided in the front surface of the containment device. Then, air that passed through the filter inside the filter unit returns to the temperature and humidity control device via the third connection means.

That is, air whose temperature and humidity are controlled circulates through the temperature and humidity control device, the containment device, and the filter unit, and passes through only these limited spaces. The temperature and humidity inside the containment device are controlled, so that the flow rate of the air can be reduced. Accordingly, the airflow in the work space weakens, and the measured value of the installed scale becomes stable.

Hazardous particles floating in the work space according to a measuring operation stay in the containment device, the second connection means, and the filter unit, so that the particles are reliably contained in the measuring system and an operator can be prevented from being exposed to the particles.

The closed space of this measuring system is complete in the temperature and humidity control device, the containment device, and the filter unit, so that the system can be made small, and requires no expansion construction beyond this system. In addition, the system has a configuration in which the temperature and humidity control device, the containment device, and the filter unit are separate from each other, and these are connected to each other, so that new installation, movement, and retrofit of the system are also easy.

Preferably, the air inlet of the containment device is provided on an upper surface of the containment device, and the air outlet is provided on either of the left and right side surfaces of the containment device.

With this configuration, a down-flow flowing from the upper side to the lower side is generated in the work space, and flow rate controllability and air agitation performance around the measuring equipment as an essential point are improved.

Preferably, an upper horizontal baffle that has a vent hole and controls the airflow is provided at an upper position in the work space.

With this configuration, air that flowed into the work space streams down on an upper surface of the upper horizontal baffle and flows from the vent hole, so that the airflow path inside the work space becomes a laminar flow with respect to the scale, and the measured value can be stabilized.

Preferably, the vent hole is formed at a position except for a region below the air inlet of the containment device.

With this configuration, air in a stage where its wind velocity is relatively high after being blown out from the air inlet reliably hits the upper horizontal baffle and is weakened, and then flows, so that the measured value can be further stabilized.

Effect of the Invention

According to the present invention, a measuring system with which hazardous fine particles can be stably, safely, and easily measured can be provided.

EMBODIMENTS FOR IMPLEMENTING INVENTION

Next, a preferred embodiment of the present invention will be described with reference to the drawings.

FIG. 1 is a right perspective view of a measuring system according to the embodiment.

A measuring system 10 includes a temperature and humidity control device 11, a filter unit 12, a containment device 13 having a work space 3, a first duct 14, a second duct 15, and a third duct 16. The containment device 13 is mounted on a workbench that is not a component of the measuring system 10. In the work space 3, a scale 5 is installed. The scale 5 is not a component of the measuring system 10, has reading accuracy of measured value (minimum indication unit) of 1 μm (0.001 mg), and is suitable for measurement of hazardous particles such as PM2.5.

The temperature and humidity control device 11 is used for the work space 3 to realize set temperature and humidity. The temperature and humidity control device 11 includes an intake port 112 and a discharge port 113. The temperature and humidity control device 11 includes a cooler, a heater, and a humidifier inside a housing of the device, and at an inner end opening of the discharge port 113, a blast fan 18 that is capable of controlling a flow rate, and blows air controlled in temperature and humidity toward an outer end opening of the discharge port 113, is disposed. A temperature and humidity environment in the work space 3 is detected by a temperature and humidity sensor installed in the work space 3. The temperature and humidity of taken-in air from the intake port 112 is adjusted to the set temperature and humidity by, for example, PID control.

The filter unit 12 is used for removing hazardous particles from air discharged from the work space 3. The filter unit 12 has an intake vent hole 122 and a discharge vent hole 123. Inside the housing of the filter unit 12, a single or a plurality of filters capable of collecting particles are incorporated.

As the filter, a HEPA filter (High Efficiency Particulate Air Filter) or, depending on hazardousness of particles to be handled, an ULPA filter (Ultra Low Penetration Air Filter) is preferably used. A HEPA filter is prescribed as "air filter having a collection efficiency of 99.97% or more with respect to 0.3 μm particles at a rated air volume, and an initial pressure loss of 245 Pa or less" in JIS 28122. An ULPA filter is prescribed as an "air filter having a particle collection efficiency of 99.9995% or more with respect to particles with particle diameters of 0.15 μm at a rated air volume, and an initial pressure loss of 245 Pa or less" by the same standards. The filter unit 12 has a structure called a bag-in bag-out system, capable of being safely replaced without directly touching a contaminated filter.

In such a case where the volume of the work space 3 is changed from the initial design, the filter unit 12 is preferably additionally provided with a suction fan (second blast fan) that can be controlled separately from the blast fan 18 of the temperature and humidity control device 11, at a downstream position of the filter in the airflow path. By providing the second blast fan in the filter unit 12, suctioning air by a blast force of the second blast fan, and forcing the air to pass through the filter, the flow rate of the particles to be collected by the filter can be optimally controlled as an air flow-in or flow-out amount. By controlling the second blast fan, the flow rate in the work space 3 can be adjusted, and an optimal flow rate that does not cause particles scattering to the outside of the work space 3 can be obtained.

The first duct (first connection means) 14 is used for hermetically connecting the discharge port 113 of the temperature and humidity control device 11 and an air inlet 132 (described below) of the containment device 13.

The second duct (second connection means) 15 is used for hermetically connecting an air outlet 133 (described below) of the containment device 13 and the intake vent hole 122 of the filter unit 12.

The third duct (third connection means) 16 is used for hermetically connecting the discharge vent hole 123 of the filter unit 12 and the intake port 112 of the temperature and humidity control device 11.

Each of the first duct 14, the second duct 15, and the third duct 16 is formed by a bellows type tubular body that can expand and contract, and deform by bending.

Next, the containment device 13 will be described. FIG. 2 is a front view of the containment device, FIG. 3 is a plan view of the containment device, FIG. 4 is a left side view of the containment device, and FIG. 5 is a longitudinal sectional view (sectional view taken along V-V line in FIG. 2) of the containment device. Dashed lines in the figures show members that can be seen through the device because this device is transparent, or show thicknesses of the members.

The containment device 13 has the work space 3 in which measuring equipment such as a scale 5 (shown by dashed lines) and a viscometer, etc., can be installed, and is used for containing a measuring object to prevent it from flowing out to the outside of the work space 3.

The containment device 13 defines the work space 3 by the front surface 13$f$, the back surface 13$b$, the left side surface 13$l$, the right side surface 13$r$, the upper surface 13$u$, and the floor surface 13$d$. The portions other than an open section 134 provided in the front surface 13$f$, the air inlet 132 provided on the upper surface 13$u$, and the air outlet 133 provided on the left side surface 13$l$, are closed by adhesion. In the work space 3, a temperature and humidity sensor to grasp the temperature and humidity in this space is installed at an arbitrary position.

All components described below, except for the floor surface 13$d$, of the containment device 13 are preferably made of a transparent resin. In the embodiment, all components are made of acrylic resin so that a contamination status can be confirmed at a glance.

The back surface 13$b$ and the floor surface 13$d$ of the containment device 13 are formed of a board made of the above-described resin.

The upper surface 13$u$ of the containment device 13 is formed of a board made of the above-described resin. The air inlet 132 having a truncated-cone tubular shape is integrally formed at a rear side central portion of the device. A front side portion 13$uf$ of the upper surface 13$u$ is curved obliquely downward.

The front surface 13$f$ of the containment device 13 is formed so that a board made of the above-described resin is divided into an upper portion 13$fu$ and a lower portion 13$fd$, and the portion between the upper portion 13$fu$ and the lower portion 13$fd$ is the open section 134. The containment device 13 has the open section 134 in the front surface 13$f$ of the work space 3 on the operator operation side, so that a measuring operation can be easily performed. The open section 134 is preferably formed so as to occupy an area substantially ⅓ of the whole area of the front surface 13$f$ from the viewpoint of securing workability and prevention of flow out of air to the outside.

The upper portion 13$fu$ is fixed acting as an opening door capable of opening and closing to the front side portion 13$uf$ by a hinge. The upper portion 13$fu$ is fixed to the upper surface 13$u$ so as to incline substantially 30° forward of the device from the device up-down direction. An open section side end portion 13$fu$E of the upper portion 13$fu$ is smoothly bent toward the inside of the device and rounded.

The lower portion 13$fd$ is also fixed to the floor surface 13$d$ so as to incline substantially 30° forward of the device from the device up-down direction. An open section side end portion 13$fd$E of the lower portion 13$fd$ is also smoothly bent toward the inside of the device and rounded.

The left side surface 13$l$ of the containment device 13 is formed so that a rectangular opening 135 for attachment of the air outlet 133 is formed at a position that is a substantially central portion in the device front-rear direction and below the upper portion 13$fu$ (opening door) of the front surface 13$f$ in the device up-down direction on a board made of the above-described resin. At the corners of the opening 135, screw holes are respectively formed. The air outlet 133 is cylindrically formed integrally with a resin-made intake port plate 136 formed to be slightly larger than the opening 135. In the intake port plate 136, screw holes are also formed at positions corresponding to those at the corners, and the opening 135 is covered by the intake port plate 136 from the outside of the device, and screwed and closed from the outside of the device.

In the left side surface 13$l$, an opening 137 for cables is formed at a lower portion on the device rear side. The opening 137 for cables is an opening for allowing electric communication cables necessary for measuring equipment out of the containment device 13. To the inside of the device, a cable lid 138 that covers the opening 137 for cables is screwed turnably. The opening 137 for cables is closed by the cable lid 138 inside the device.

At a open section side end portion 13$l$E of the left side surface 13$l$, a front baffle 20L that extends in the device up-down direction along the open section 134 is attached.

The front baffle 20L is a resin plate having a smooth bent portion in the short direction of the resin plate, and is provided to control airflow. The front baffle 20L is fixed to the open section side end portion 13$l$E so that one surface is contact with the inside of the left side surface 13$l$ and screwed from the outside of the left side surface 13$l$, and the other surface extends to the right side of the device from the open section side end portion 13$l$E. By the front baffle 20L, the open section side end portion 13$l$E of the left side surface 13$l$ is rounded.

The right side surface 13$r$ of the containment device 13 has the structure similar to that of the left side surface 13$l$, and has an opening 135, an opening 137 for cables, and a cable lid 138. That is, the intake port plate 136 in which the air outlet 133 is formed is provided on each of the left side surface 13$l$ and the right side surface 13$r$. In the embodiment, the opening 135 that is not used for the right side surface 13$r$ is closed by a closing plate instead of the intake port plate 136. At an open section side end portion 13$r$E of the right side surface 13$r$ as well, a front baffle 20R that is for the same purpose, has a similar shape, and extends from the inside of the right side surface 13$r$ to the left side of the device is also attached, and by the front baffle 20R, the open section side end portion 13$r$E of the right side surface 13$r$ is rounded.

In the work space 3 of the containment device 13, an upper horizontal baffle 30 is fixed. FIG. 6 is a perspective view of the upper horizontal baffle.

The upper horizontal baffle 30 is a board made of the above-described resin, having a size substantially corresponding to the upper surface 13$u$ and provided to control airflow. Left and right end portions of the upper horizontal baffle 30 are bent vertically upward from the baffle extending surface, and serve as attaching portions 31. In each attaching portion 31, screw holes are formed at a plurality of positions at even intervals. In the left side surface 13*l* and the right side surface 13*r*, screw holes are formed at positions corresponding to the screw holes of the attaching portions 31 at a height substantially equal to the fixing height of the upper portion 13*fu*. The upper horizontal baffle 30 is screwed from the outside of the device and fixed horizontally to an upper position of the work space 3.

In a device front region 30*f* of the upper horizontal baffle 30, a plurality of vent holes 32 are formed. Each of the vent holes 32 is formed into a thin and long rectangular shape with rounded nonangular end portions, and in the device front region 30*f*, four vent holes in total are formed at even intervals in two lines in the device left-right direction and two lines in the front-rear direction.

Next, operation of the measuring system 10 configured as described above will be described. FIG. 7 is a schematic view of airflow in a front view of the containment device, and FIG. 8 is a schematic view of airflow in a right side view of the containment device. The arrows in the figures represent airflow.

When the temperature and humidity control device 11 is started, by the blast fan 18 inside the temperature and humidity control device 11 and the second blast fan inside the filter unit 12 operated as necessary, air controlled to set temperature and humidity is guided into the containment device 13 from the discharge port 113 via the first duct 14, and flows into the work space 3 from the air inlet 132. At this time, in the work space 3, by controlling the blast fan 18 (second blast fan as necessary) in advance, designed airflow is generated, and a negative pressure relative to the outside of the measuring system is generated in the open section 134 of the containment device 13 which is the only open space of the measuring system 10. Therefore, air that has passed through the work space 3 and been contaminated is discharged from the air outlet 133 together with the outside air that flowed into the work space 3 from the open section 134, and guided from the intake vent hole 122 to the filter unit 12 via the second duct 15. Air from which particles were collected and removed by passing through the filter inside the filter unit 12 is fed out from the discharge vent hole 123, and returns to the temperature and humidity control device 11 from the intake port 112 via the third duct 16. The returned air is controlled to set temperature and humidity and recirculated to the work space 3.

At this time, since all of the surfaces surrounding the open section 134 are rounded to be nonangular, air flowing in from the open section 134 is taken as a laminar flow into the work space 3 without becoming a turbulent flow.

Air that has entered the work space 3 from the air inlet 132 has a comparatively high wind velocity, however, the air reliably hits a device rear region 30*b* of the upper horizontal baffle 30 which is disposed in a lower region of the air inlet 132, and is reduced in wind velocity. Then, the air streams on the upper surface of the upper horizontal baffle 30 and becomes a breeze down-flow flowing down from the vent holes 32 of the device front region 30*f* and flows in the work space 3.

As described above, according to the measuring system 10 of the embodiment, in the work space 3, the flow path of air whose temperature and humidity are controlled becomes a laminar flow with respect to the scale 5, so that the measured value of the scale 5 becomes stable.

According to the measuring system 10, the air flow rate in the work space 3 can be reduced to 6 [m$^3$/min] by the above-described flow path design and configuration in which air is circulated only in a limited space in the temperature and humidity control device 11, the containment device 13, and the filter unit 12.

By adopting a down-flow in a flow path design of the measuring system 10, the flow rate controllability and air agitation performance around the scale 5 serving as an essential point are improved. That is, a configuration in which an up-flow is formed in the work space 3 by providing the air outlet 133 on the upper surface 13*u* of the containment device 13 is also possible, however, due to the up-flow, a large amount of air that entered from the open section 134, the air is in a stage where its wind velocity is comparatively high, hits the periphery of the scale 5 serving as an essential point and makes flow rate control difficult, and in addition, in the work space 3, air agitation performance is higher in the case of down-flow than in the case of up-flow, so that from the viewpoint of stable measurement, down-flow is preferable.

Hazardous particles that float in the work space 3 according to a measuring operation stay inside the containment device 13, the second duct 15, and the filter unit 12, so that the particles are contained inside the measuring system 10. At this time, air is not refluxed to the outside of the measuring system 10 but circulated inside the measuring system 10, and the outside air is positively flowed in from the open section 134, so that the particles are reliably contained.

In this measuring system 10, a final contamination region is limited within the second duct 15 and the filter unit 12, so that exposure of an operator during the replacement operation can be reduced by integrally replacing the second duct 15 and the filter unit 12 after the operation of the system is stopped.

The closed space configured by the measuring system 10 is completely configured with the temperature and humidity control device 11, the containment device 13, and the filter unit 12, so that the measuring system 10 can be made very small as compared with a scale chamber or the like, and does not be performed expansion construction such as new provision of an exhaust pipe that a draft chamber needs, at the time of installation of the device.

Since the measuring system 10 is small in size, in addition, is constructed so that the temperature and humidity control device 11, the containment device 13, and the filter unit 12 are configured as separate units, and are connected by the ducts 14, 15, and 16, these units can be flexibly arranged, and new installation, movement, and retrofitting of the system are easy and the degree of freedom of installation is high.

REFERENCE SIGNS LIST

Figure 1:
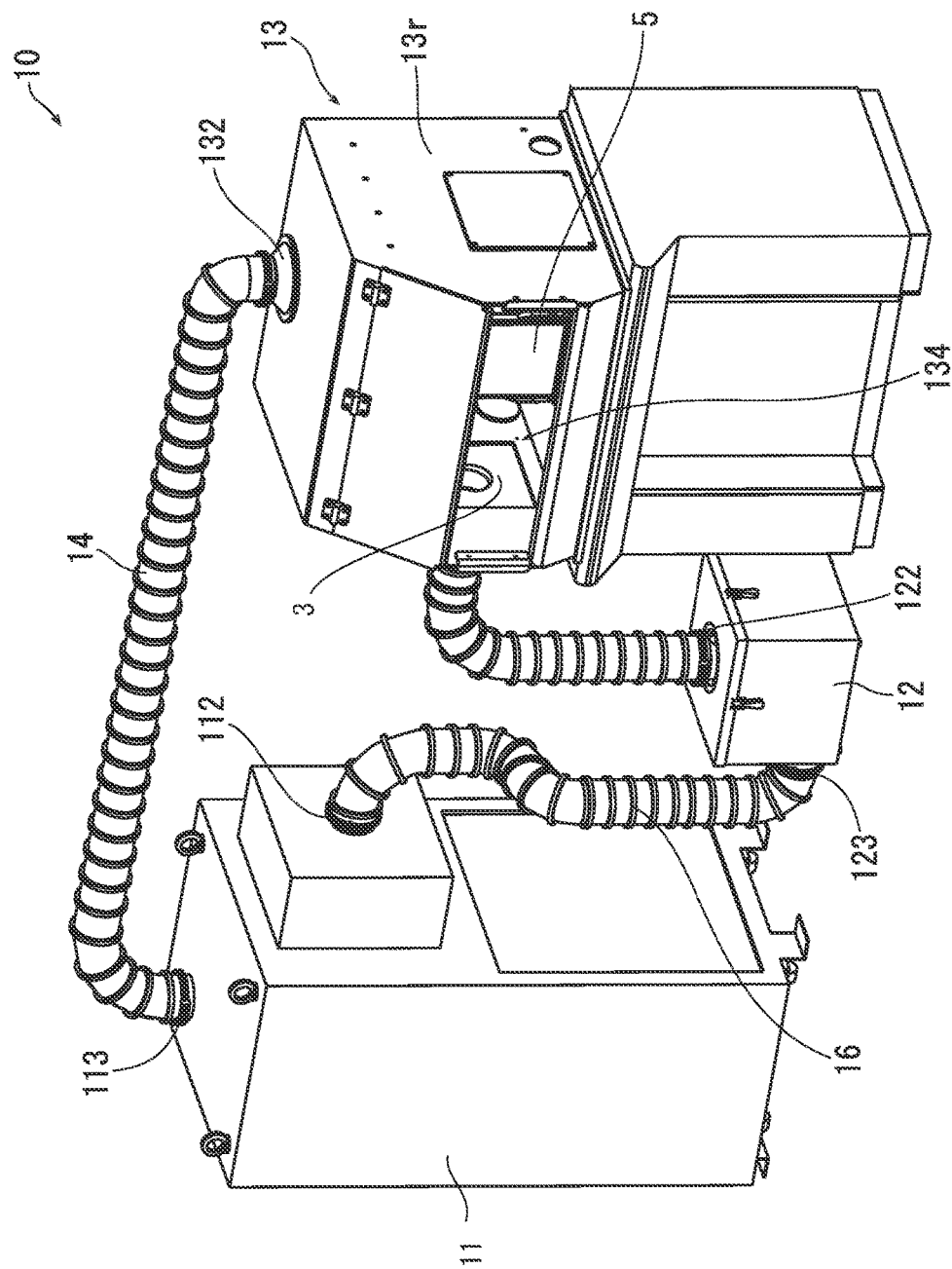
FIG. 1 is a right perspective view of a measuring system according to the embodiment.
Figure 2:
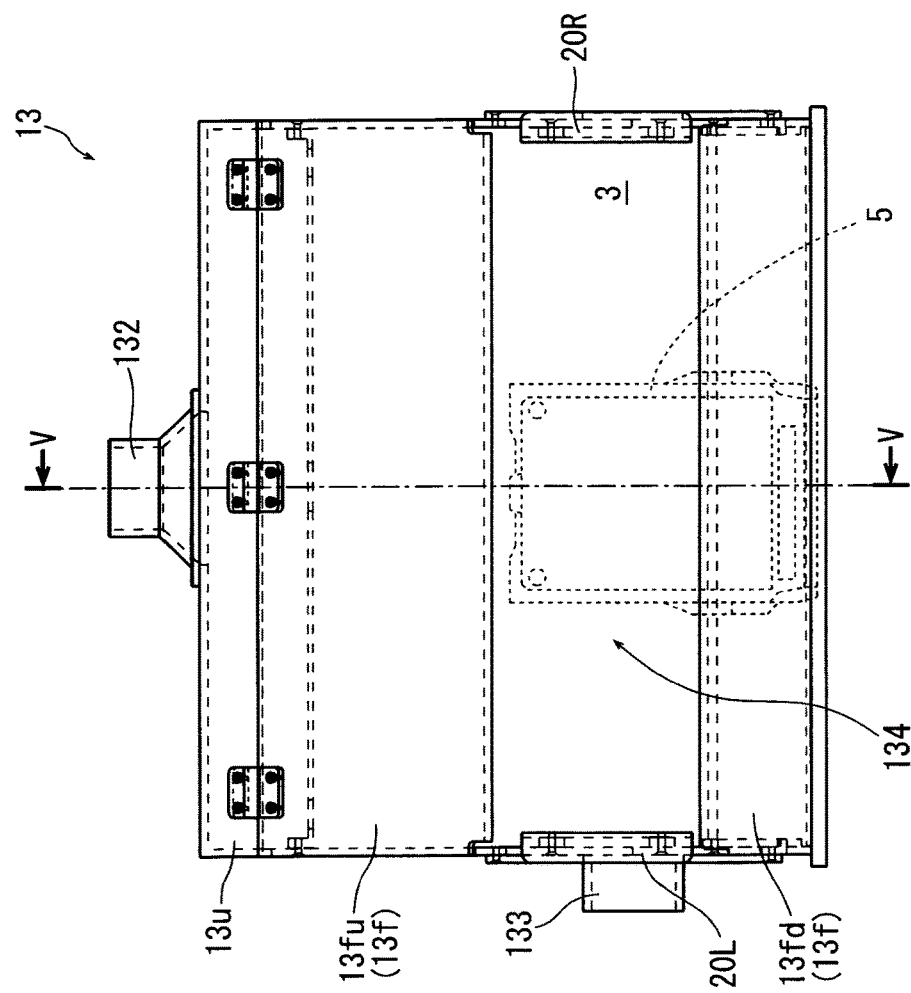
FIG. 2 is a front view of a containment device.
Figure 3:
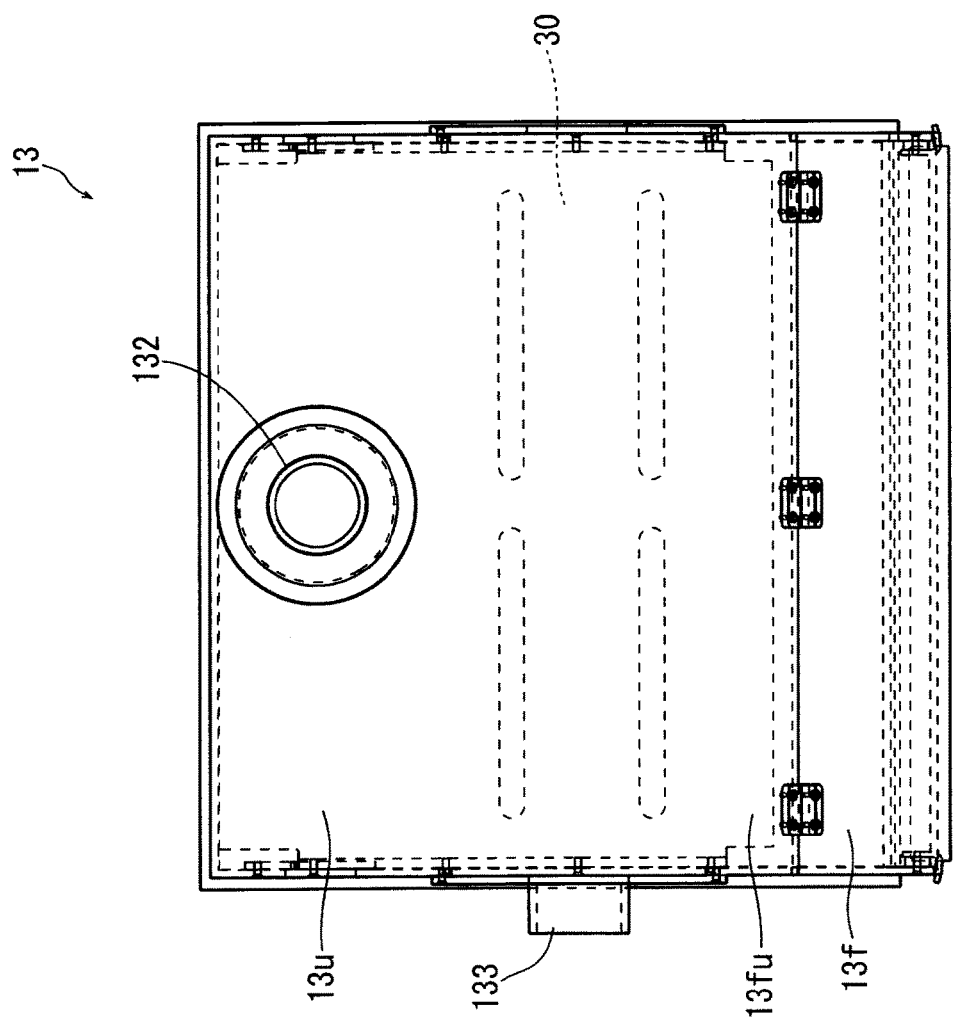
FIG. 3 is a plan view of the containment device.
Figure 4:
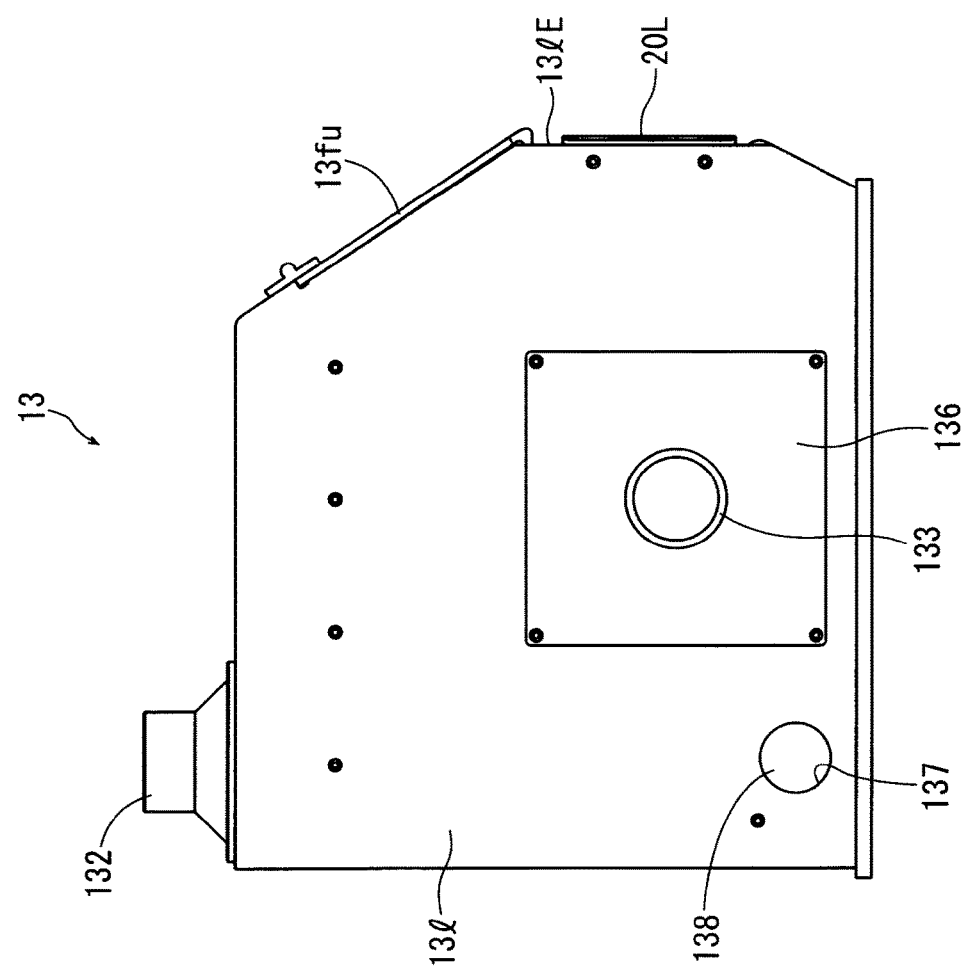
FIG. 4 is a left side view of the containment device.
Figure 5:
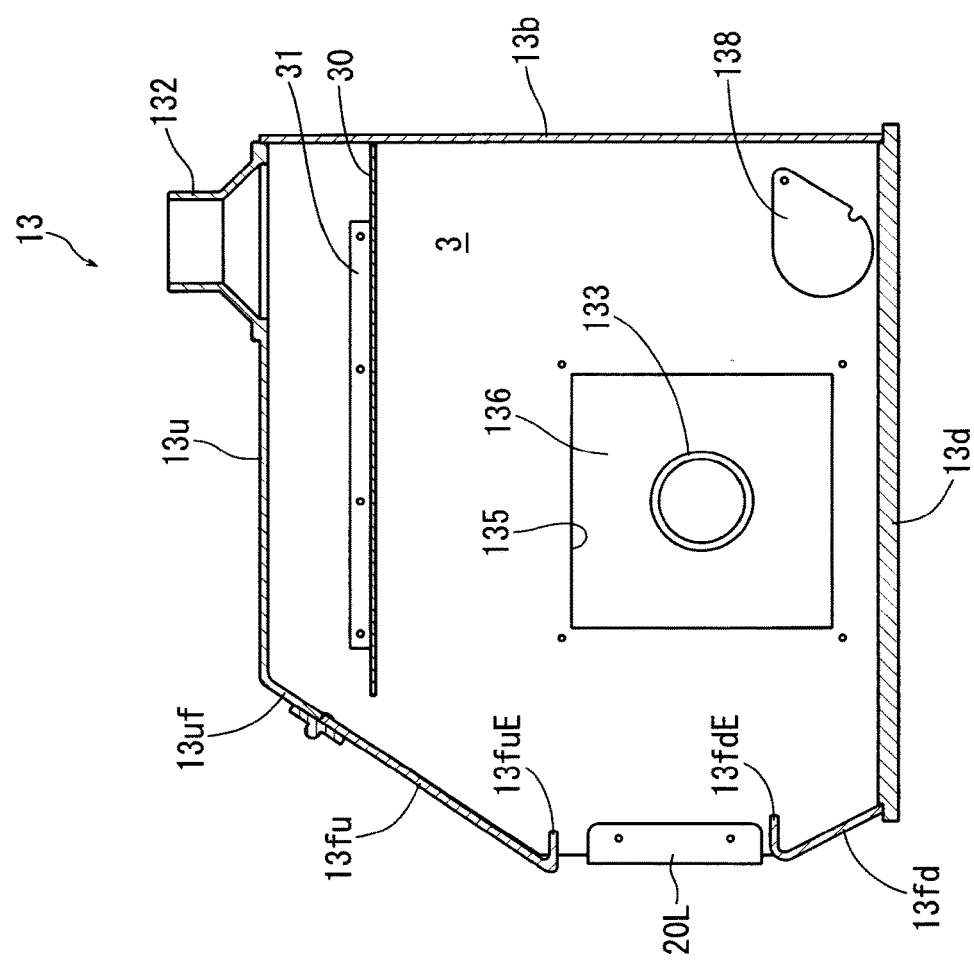
FIG. 5 is a longitudinal sectional view (sectional view taken along V-V line in FIG. 2) of the containment device.
Figure 6:
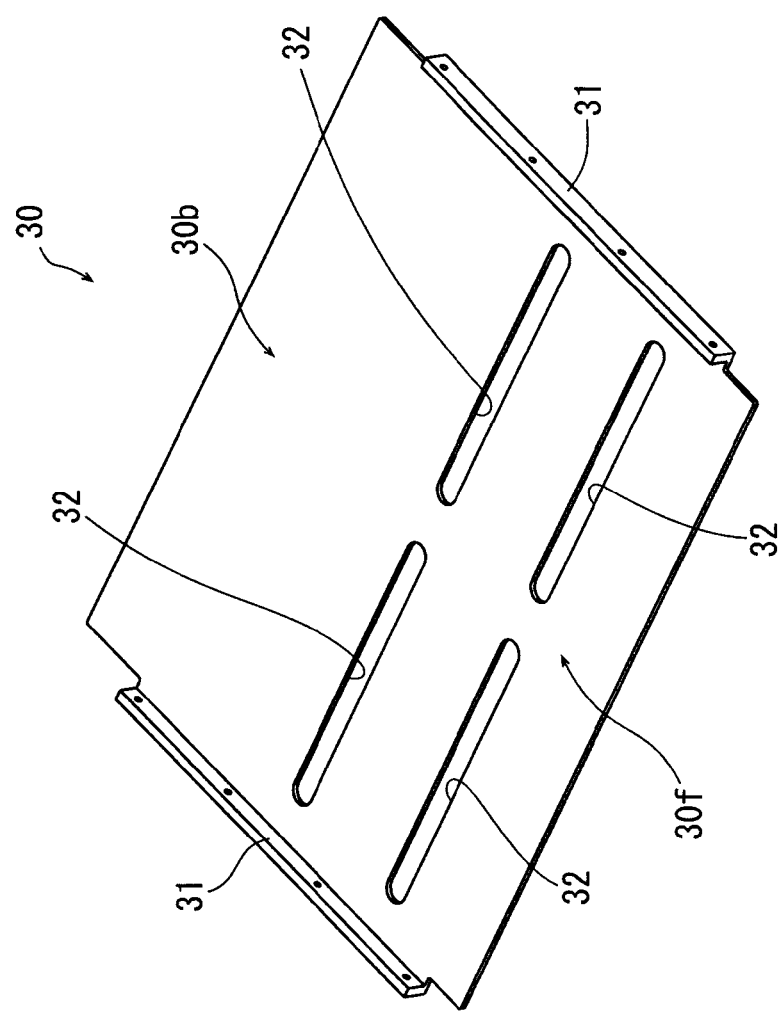
FIG. 6 is a perspective view of an upper horizontal baffle.
Figure 7:
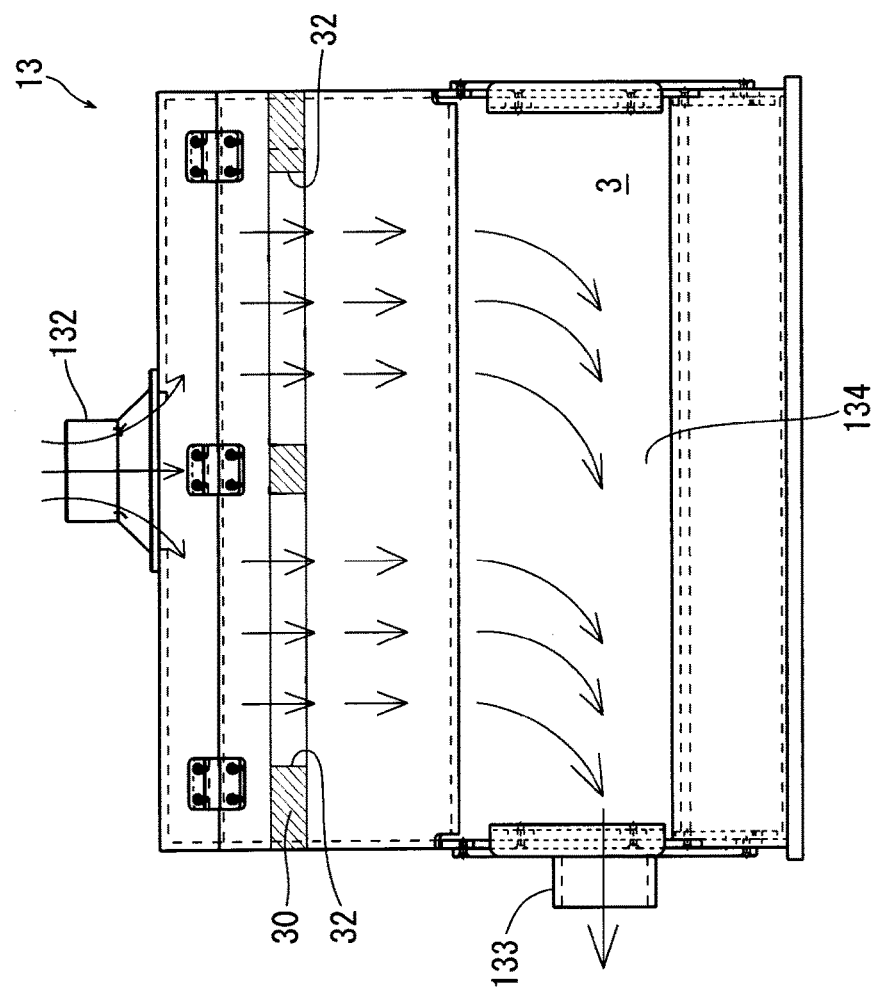
FIG. 7 is a schematic view of airflow in a front view of the containment device.
Figure 8:
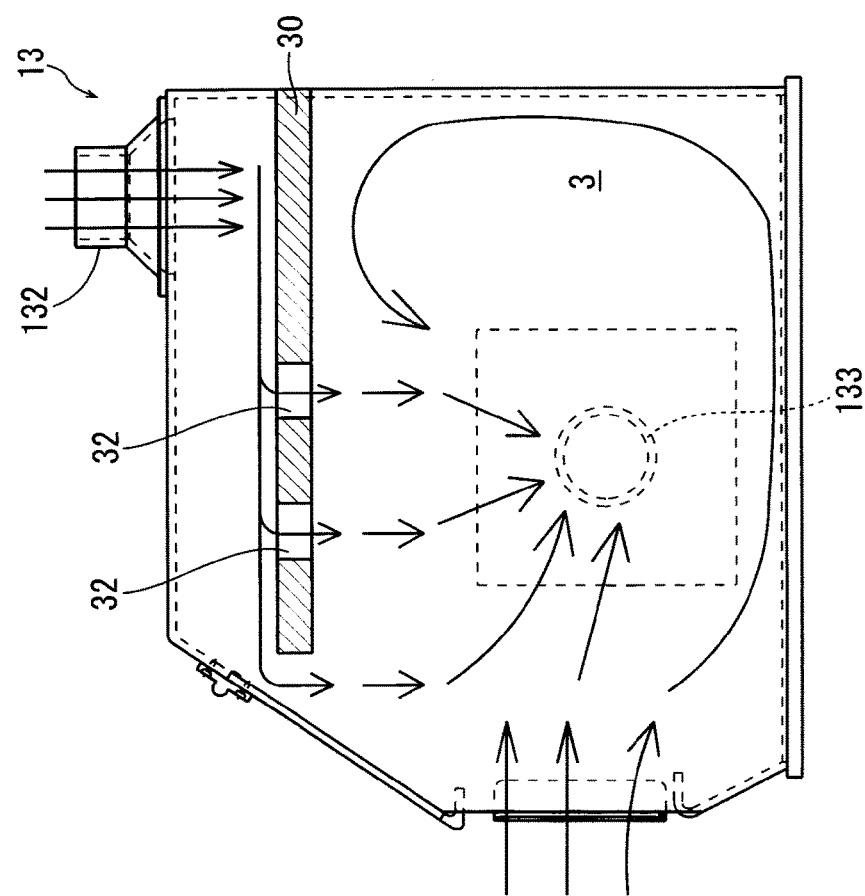
FIG. 8 is a schematic view of airflow in a right side view of the containment device.
Figure 9:
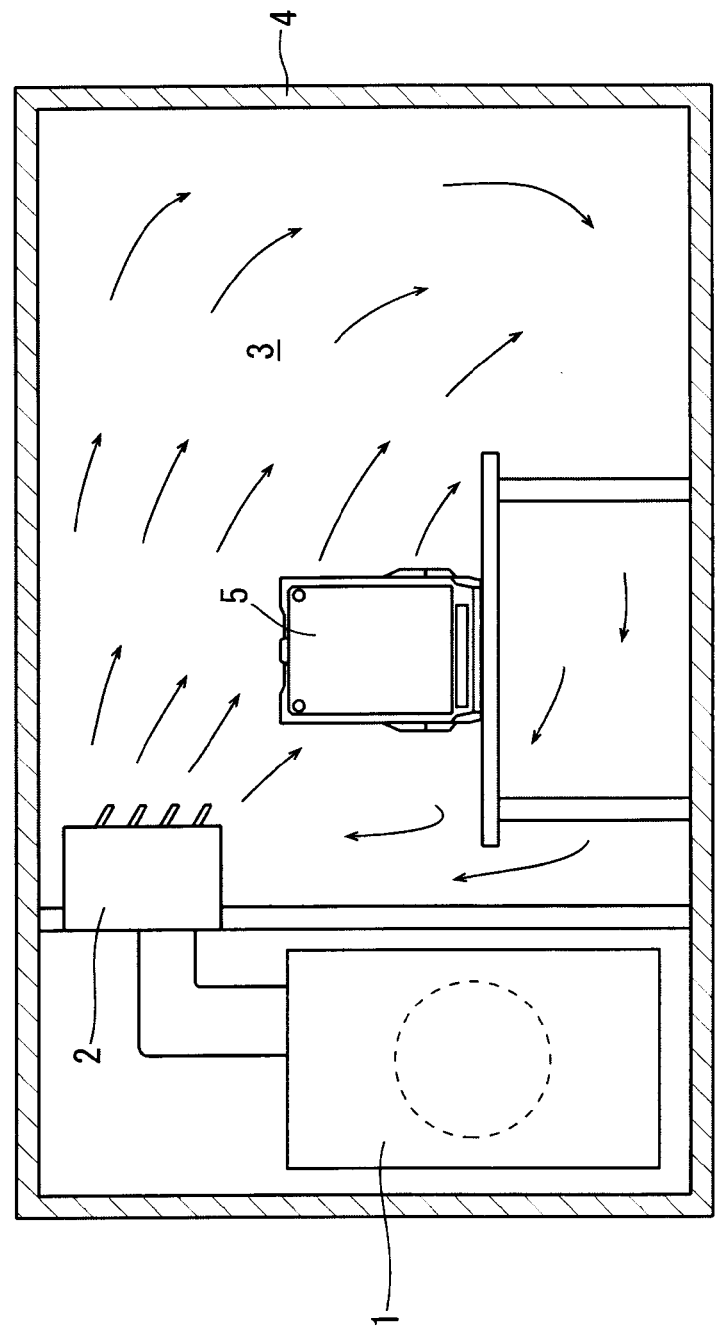
FIG. 9 is a view describing a conventional scale chamber.

5 Scale
10 Measuring system

11 Temperature and humidity control device
112 Intake port
113 Discharge port
12 Filter unit
122 Intake vent hole
123 Discharge vent hole
13 Containment device
13f Front surface
13l Left side surface
13r Right side surface
13u Upper surface
132 Air inlet
133 Air outlet
134 Open section
14 First duct (first connection means)
15 Second duct (second connection means)
16 Third duct (third connection means)
18 Blast fan
20L, 20R Front baffle
30 Upper horizontal baffle
32 Vent hole

The invention claimed is:

1. A containment workstation comprising:
a work space in which measuring equipment can be installed;
a containment device that defines the work space by closing portions other than an open section provided in the front surface of the work space, and an air inlet and an air outlet set in the work space;
a temperature and humidity control device that controls a temperature and a humidity of taken-in air and can blow the air into the work space;
a filter housing that has a filter capable of collecting particles;
a first duct that hermetically connects the temperature and humidity control device and the air inlet of the containment device;
a second duct that hermetically connects the air outlet of the containment device and the filter housing; and
a third duct that hermetically connects the filter housing and the temperature and humidity control device, wherein
an upper horizontal baffle that has a vent hole and controls an airflow is provided at an upper position in the work space,
the air inlet of the containment device is provided on an upper surface of the containment device, and the air outlet is provided on either of the left and right side surfaces of the containment device in the work space lower than the upper horizontal baffle, and provided at a position central in the device front-rear direction and the device up-down direction of the side surface.

2. The containment workstation according to claim 1, wherein the vent hole is formed at a position except for a region below the air inlet of the containment device.

3. The containment workstation according to claim 1, wherein the air inlet of the containment device is provided on an upper outer surface of the containment device.

* * * * *